United States Patent [19]

Lindkvist

[11] Patent Number: 4,794,921

[45] Date of Patent: Jan. 3, 1989

[54] METHOD AND APPARATUS FOR ADMINISTERING ANESTHETICS

[76] Inventor: Erik A. Lindkvist, Korpralsvägen 38, S-902 53 Umea, Sweden

[21] Appl. No.: 739,812

[22] Filed: May 31, 1985

Related U.S. Application Data

[63] Continuation-in-part of Ser. No. 414,357, filed as PCT SE81/00383 on Dec. 18, 1981, published as WO82/01999 on Jun. 24, 1982, abandoned.

[30] Foreign Application Priority Data

Dec. 18, 1980 [SE] Sweden .............................. 8008962-6

[51] Int. Cl.$^4$ ............................................ A61M 16/00
[52] U.S. Cl. .................................................. 128/203.29
[58] Field of Search ...................... 128/207.13, 203.29, 128/910, 911, 205.25, 206.12, 206.15, 206.18, 206.21, 206.24, 206.28, 207.13, 139

[56] References Cited

U.S. PATENT DOCUMENTS

| | | | |
|---|---|---|---|
| 2,859,798 | 11/1955 | Hudson | 128/146 |
| 3,856,051 | 12/1974 | Bain | 128/911 |
| 4,265,239 | 5/1981 | Fischer, Jr. et al. | 128/910 |

FOREIGN PATENT DOCUMENTS

| | | | |
|---|---|---|---|
| 8002171 | 3/1980 | Sweden . | |
| 492723 | 9/1938 | United Kingdom | 128/207.13 |
| 490499 | 2/1978 | United Kingdom | 128/910 |

Primary Examiner—Edward M. Coven
Assistant Examiner—Reichle K. M.
Attorney, Agent, or Firm—Fleit, Jacobson, Cohn & Price

[57] ABSTRACT

A method and apparatus for reducing the atmospheric contamination in an operating room as a result of anesthetic gas that escapes from an anesthetic gas mask. The mask has a double wall structure and includes a deflector positioned within the mask body to cause turbulent flow of anesthetic gas therewithin so that the gas is substantially confined within the inner mask cavity and does not escape directly outwardly from the mask opening when the mask is removed from the face of the patient. The double wall construction provides an extraction slot around the inner mask body that is in communication with a source of reduced pressure to extract any anesthetic gas that escapes from within the inner mask body. A connector is provided for supplying anesthetic gas, for withdrawing exhaled gas.

23 Claims, 9 Drawing Sheets

METHOD AND APPARATUS FOR ADMINISTERING ANESTHETICS

CROSS-REFERENCE TO RELATED APPLICATION

This application is a continuation-in-part of co-pending application Ser. No. 414,357, filed as PCT SE81/00383 on Dec. 18, 1981, published as WO82/01999 on Jun. 24, 1982, now abandoned.

BACKGROUND OF THE INVENTION

1. Field of the Invention

The present invention relates to a method and apparatus for minimizing the escape of anesthetic gas into the atmosphere surrounding a patient being administered gaseous anesthesia. More particularly, the present invention is directed to a method and apparatus for collecting anesthetic gases that escape from an anesthetic mask adjacent the point at which they are introduced in order to minimize contamination of the ambient atmosphere with anesthetic gases.

2. Description of the Prior Art

The administration of anesthetic gases to a patient is frequently accomplished by means of a mask that is applied over the nose or the mouth, or both, of the patient in order to provide controlled introduction of the anesthetic gas to the patient without subjecting others around the patient to the direct flow of the gases. However, anesthetic gases frequently leak into and contaminate the atmosphere surrounding the patient, for a number of reasons, and thereby expose the anesthetist and others in the vicinity of the patient to those same anesthetic gases. Such leakage of anesthetic gas can be the result of leakage at the various joints and connections in the gas delivery system, the result of improper fit of the mask to the face of the patient, or the result of escape of gas by virtue of the periodic removal of the mask from the face of the patient to permit visual observation of the patient's nose and mouth, and thereby detect changes in color of the patient's lips and possible vomiting. All of those causes of leakage contribute to contamination by anesthetic gas of the atmosphere in the operating theatre. Such contamination exposes the anesthetist, the surgeons, and the nurses who are present in the operating theatre to those same anesthetic gases, which, even though in a less concentrated form, could, over a period of time, impair their effectiveness.

The National Institute of Occupational Safety and Health has recognized the possible adverse effects on anesthetists and others of extended exposure to anesthetic-contaminated air and has recommended an upper limit for the amount of such anesthetics in the operating theatre atmosphere. For example, tests have shown that the concentration of nitrous oxide anesthesia in the immediate breathing zone of the anesthetist in an operating theatre could range from 45 to 500 ppm, with a mean value of 145+/−29 ppm, by using a conventional anesthesia mask. The NIOSH has recommended an upper limit of 25 ppm. In that connection, the ordinary air conditioning and ventilation system in hospital operating rooms is insufficient to control the anesthesia level in the atmosphere to that level, particularly in the localized area in the immediate vicinity of the patient and anesthetist. Consequently, it has been suggested that a local gas collection system be utilized, wherein a nozzle or collector is placed close to the patient's face and is connected to an evacuation fan to withdraw the anesthesia gases that have escaped. However, because access to the patient's face from above must be maintained, such systems place the collection nozzle on the side of the patient's face, where they are relatively ineffective. Additionally, the proposed systems have been found to be quite bulky, and their installation costs are high.

Another approach to minimizing the escape into the atmosphere of anesthetic gases is to provide a double wall mask wherein the space between the walls is connected with a source of vacuum and defines an extraction passageway to collect and remove anesthetic gas that escapes between the inner mask and the face of the patient, as shown in U.S. Pat. No. 4,015,598, granted on Apr. 1, 1977, to Glenn E. Brown. However, the structure therein disclosed is of limited utility in that it collects anesthetic gas that leaks out between the inner mask and the patient's face, but it does not prevent the excessive escape into the atmosphere of anesthetic gas when the mask is removed from the patient's face, as is done periodically to check the patient and monitor his breathing.

There is, thus, a need for an improved means for preventing the escape into the surrounding atmosphere of anesthetic gases that are used in operating rooms in order to prevent the exposure of operating room personnel to excessively high levels of the anesthetics.

SUMMARY OF THE INVENTION

It is an object of the present invention to provide an improved anesthetic mask structure that includes means to collect anesthetic gases that would otherwise escape into the surrounding atmosphere.

It is another object of the present invention to provide an improved anesthetic mask that permits visual observation to be made of the patient's oral-nasal area without the need to remove the mask from the patient's face.

It is still another object of the present invention to provide an improved anesthetic mask structure that is of simple construction and that can easily be disassembled and reassembled for cleaning and sterilization purposes, and that is capable of reuse.

It is a further object of the present invention to provide an improved anesthetic mask structure wherein the mask is made of materials that can withstand sterilization temperatures.

It is a still further object of the present invention to provide an improved anesthetic mask structure that is relatively inexpensive, and is more effective than presently available masks to minimize the contamination with anesthetics of the atmosphere in operating rooms.

It is another object of the present invention to provide an improved anesthetic mask structure that assists in maintaining in an operating room an atmosphere that conforms with the suggested anesthesia contamination levels of the National Institute of Occupational Safety and Health.

It still another object of the invention to provide a mask connector that is configured so as to minimize the dead air space between the patient's face and the tubes that supply anesthetic gas and that withdraw exhaled gas.

It is a still further object of the present invention to provide a method of minimizing anesthetic gas contamination of the atmosphere in an operating room.

Briefly stated, in accordance with one aspect of the present invention, a double wall mask is provided for the administration of anesthetic gases. The mask includes an inner, cup-shaped mask body that defines a cup-shaped cavity and includes a flexible outer edge adapted to engage the face of the patient in substantially gas-tight sealing relationship around the oral-nasal area. The inner mask body includes an inner opening that has a central axis to permit the introduction into the mask cavity of anesthetic gas and the withdrawal therefrom of exhaled gases. An outer cup-shaped body is provided around the outside of the inner mask and has a shape that corresponds with that of the inner mask and includes an outer opening that is larger than and spaced laterally from the inner opening of the inner mask to define an extraction slot. The slot communicates with the space between the inner and outer mask bodies, and the outer body includes an inner opening that is in communication with the slot. A connecting member is positioned at the respective inner openings of the inner and outer mask bodies to hold the two bodies together at a desired spacing. The connecting member includes a passageway to permit the introduction into the mask cavity of anesthetic gas, and also includes a deflecting member positioned opposite the outlet of the passageway to deflect the anesthetic gas radially outwardly and to induce turbulence therein to cause the anesthetic gas to remain substantially within the inner cavity defined by the inner mask body. Coupling means are provided for connecting the inner mask body to a source of anesthetic gas, and to a source of vacuum to withdraw exhaled gas, and to connect the space between the inner and outer masks to an exhaust system for withdrawal of anesthetic gas that passes around the outer edge of the inner cavity and that is collected at the slot defined between the inner and outer mask bodies.

In accordance with another aspect of the present invention, a method is provided whereby anesthetic gas is introduced into a mask cavity adapted to engage with the face of the patient, and in such a way that the anesthetic gas does not stream directly out of the mask, but is confined substantially therewithin by virtue of turbulence that is induced in the gas as it is introduced into the inner mask cavity. The method includes the steps of establishing an anesthetic zone within an anesthetic mask, establishing an annular zone surrounding the anesthetic zone and having an opening that is contiguous with and surrounds the anesthetic zone, and providing anesthetic gas into the anesthetic zone at a steady rate. The method also includes the step of creating turbulence in the anesthetic gas as it is introduced into the anesthetic zone to generate eddy currents that establish a bubble of anesthetic gas adjacent the opening at which the anesthetic gas is introduced, the bubble of gas being defined in part by an inner mask cavity that has an opening adapted to engage with the face of a user, and also the step of establishing a suction pressure in the annular zone surrounding the anesthetic zone in order to collect anesthetic gas that would otherwise escape into the surrounding atmosphere.

DESCRIPTION OF THE PREFERRED EMBODIMENTS

Figure 1:
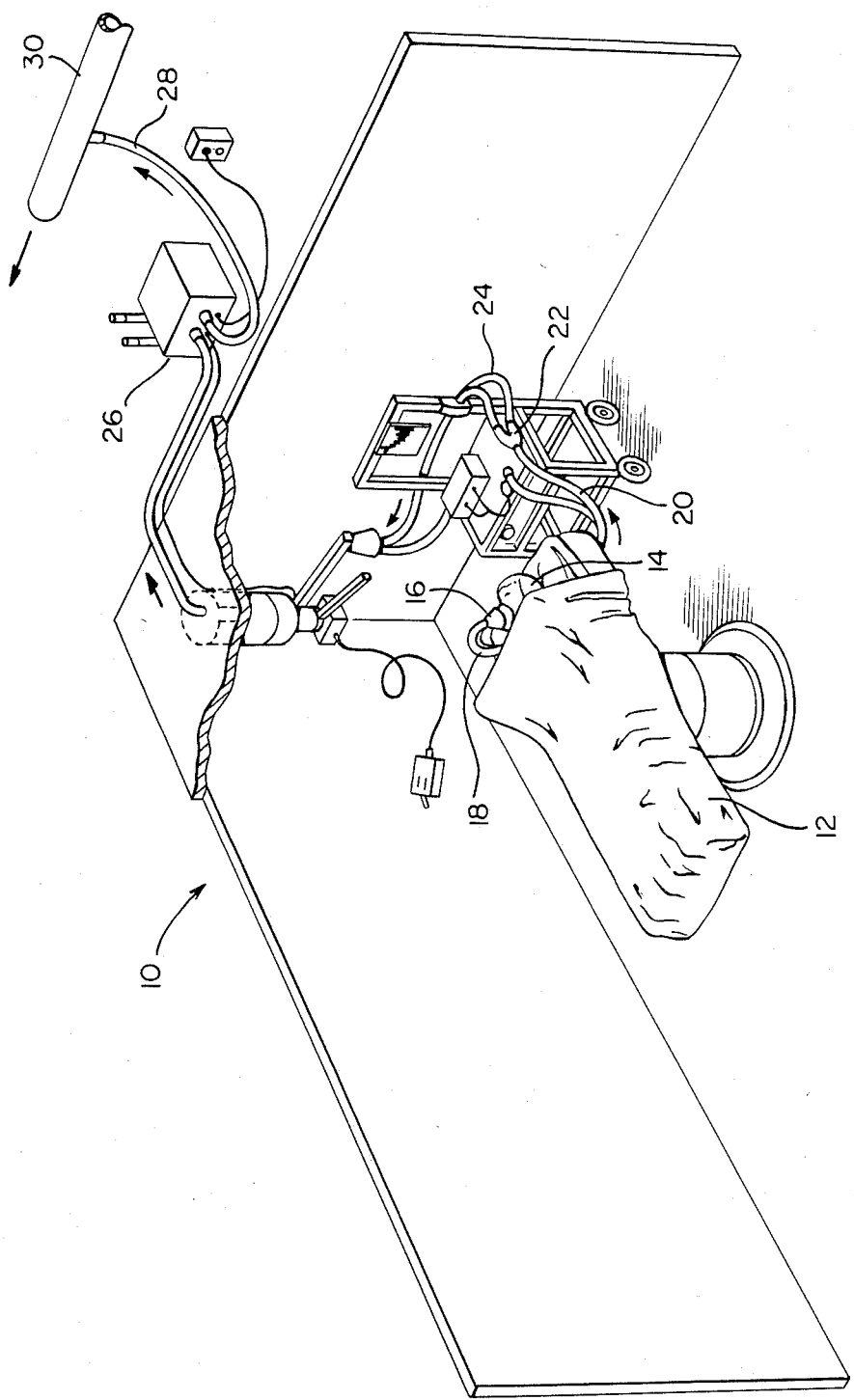
FIG. 1 is a perspective view of a part of an operating room in which the apparatus and method of the present invention can be employed and including a fixed exhaust fan for extracting leakage anesthetic gas from around the mask cavity.

Referring now to the drawings, and particularly to FIG. 1 thereof, there is shown schematically a part of an operating room 10 including an operating table 12 with a patient 14 reclining thereon, the patient having an anesthetic mask 16 of the oral-nasal variety applied over his face for the administration of anesthesia. The anesthesia is provided in pressurized gaseous form from a suitable source (not shown) and is conveyed to mask 16 through suitable connecting tubing 18. Both connecting tubing 18 and the anesthesia gas supply system can be of a conventional type that is well known to those skilled in the art, and will therefore not be described in further detail herein. Mask 16 includes a gas extraction tube 20 that is connected through a flow measurement block 22 and evacuation tubing 24 to a fixed fan assembly 26 that includes a suction fan to provide a reduced pressure to permit withdrawal of gases from around mask 16. The withdrawn gases pass from fan assembly 26 through a conduit 28 to a standard hospital extraction system 30. The flow measurement block 22 serves to control the flow of the withdrawn gases through extraction tube 20, and preferably it includes a venturi to which a flow gauge (not shown) is connected to show the rate of flow of extracted gas through extraction tube 20. The preferred rate of extraction flow through flow measurement block 22 for an adult patient is 35 m$^3$/hour while the preferred rate of extraction flow for a child-patient is 27 m$^3$/hour.

Figure 2:
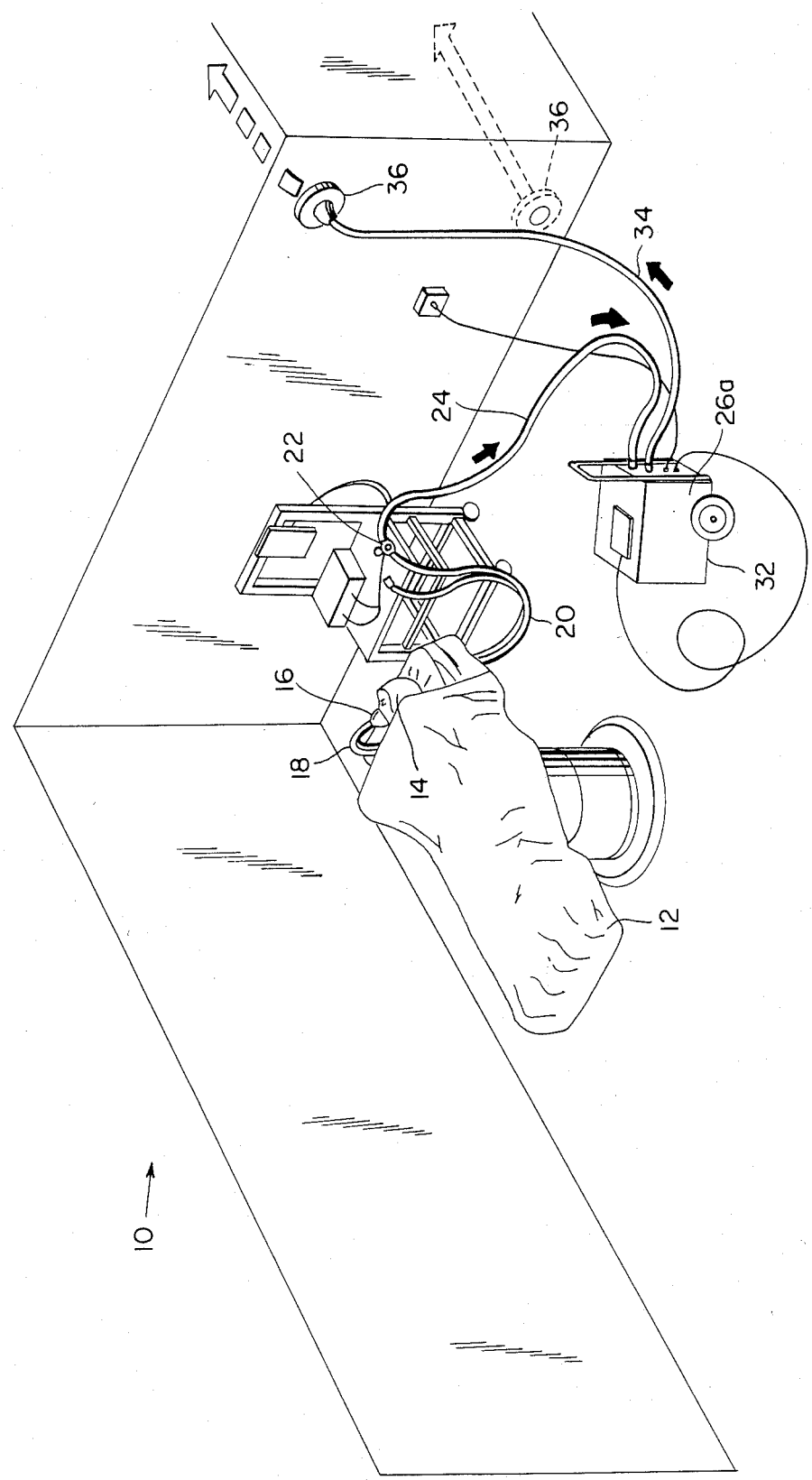
FIG. 2 is a perspective view similar to that of FIG. 1 in which the exhaust fan for withdrawing the leakage anesthetic gas from around the mask is provided in a mobile cart to permit it to be moved from one place to another.
Figure 3:
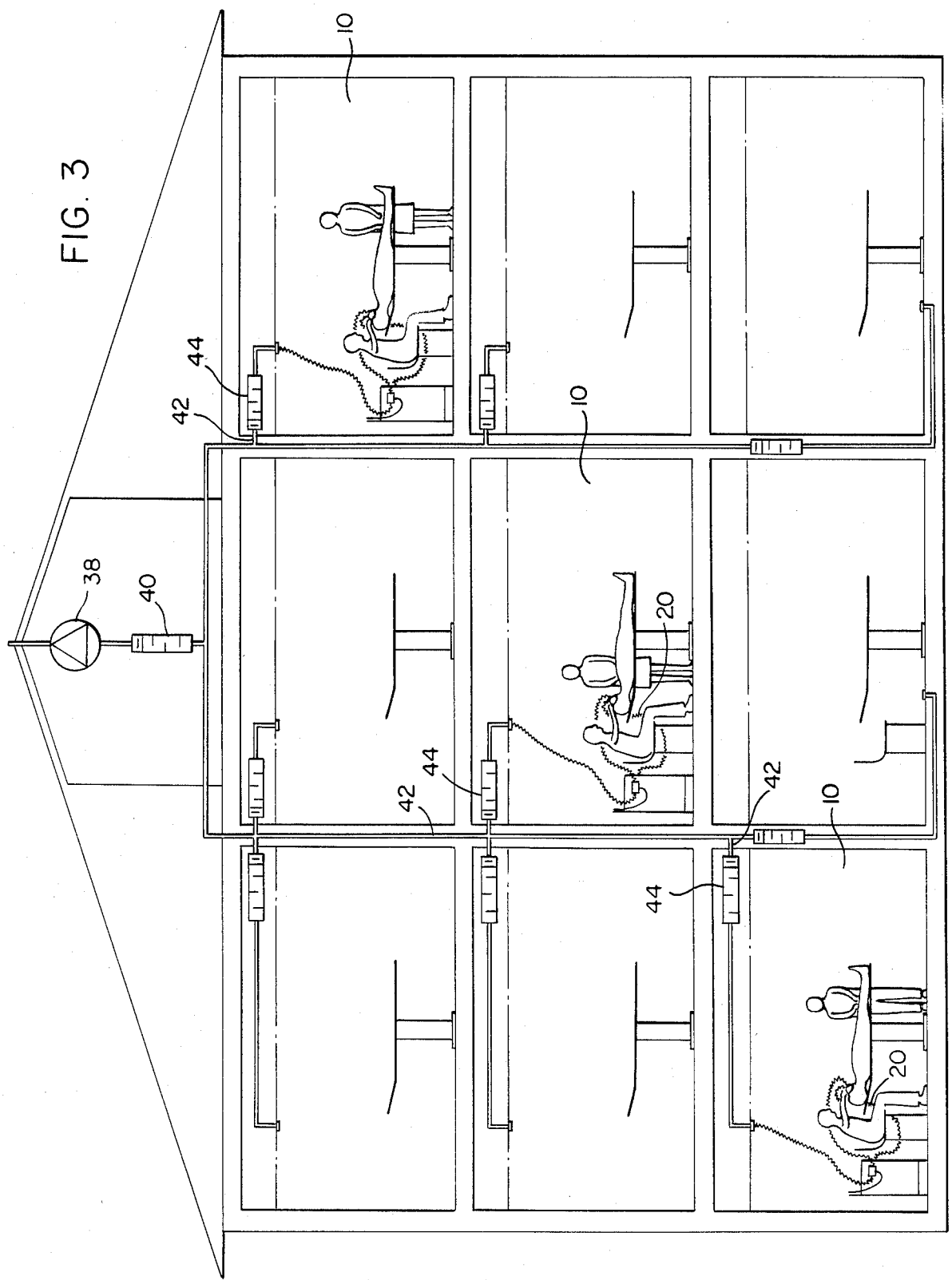
FIG. 3 is a schematic view of a multiple operating room hospital having a central evacuation system with which the method and apparatus of the present invention can be employed.

In the arrangement illustrated in FIG. 2, the extraction fan assembly 26a is provided in a mobile cart 32 that contains the fan and associated fan controls (not shown), and the exhaust from the fan is connected by conduit 34 to a suitable outlet connection 36 provided in the wall of the operating room 10. Outlet connection 36 is in communication with the hospital extraction system (not shown).

Where there are a number of such operating rooms 10, a central extraction system can be provided as illustrated in FIG. 3. As there shown, a central evacuation fan 38 is positioned in an extraction duct 40 and is in communication with each of the operating rooms 10 through suitable connecting ducting 42. Ducting 42 to each room 10 is sized to be compatible with the distance of the room from fan 38 and the capacity of the extraction tubing 20 that is provided with the mask structure in accordance with the present invention, and it includes a separate pressure and flow control valve 44 for each of the separate branch ducts that leads to one of the respective operating rooms.

Figure 4:
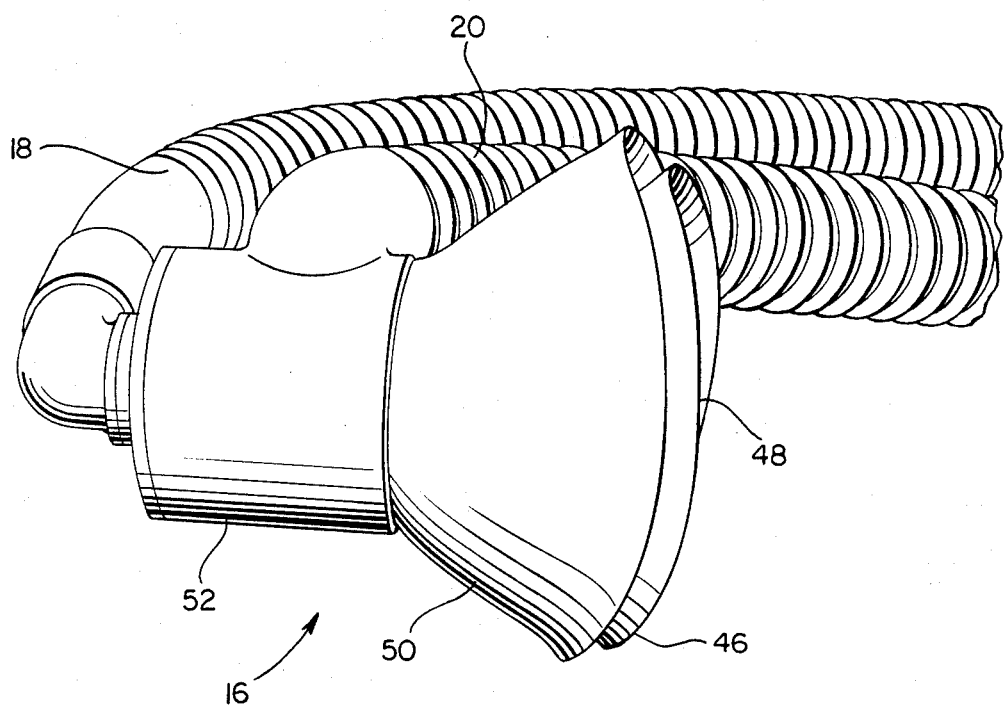
FIG. 4 is a perspective view of a double wall anesthetic mask in accordance with the present invention and including tubing for introducing the anesthetic gas, for extracting the exhaled gas, and for extracting any leakage gas that passes around the inner wall and outside of the mask.

The anesthetic mask 16 in accordance with the present invention is shown in FIG. 4 and includes an inner mask body 46 having an opening 48 adapted to fit over and enclose the oral-nasal area of the patient. An outer mask body 50 surrounds the outside of the inner mask body and is coaxial therewith, the inner and outer masks being connected to a coupling housing 52 to which a tube 18 for anesthetic gas introduction and for exhaled gas withdrawal is connected, and to which a gas extraction tube 20 is also connected. Tube 18 is adapted for communication with a source of anesthetic gas, which can be, for example, nitrous oxide, halothane, or the like, and is also in communication with a source of reduced pressure for the withdrawal of exhaled gas. Extraction tube 20 extends from coupling housing 52 to flow measurement block 22 illustrated in FIGS. 1 and 2.

Figure 5:
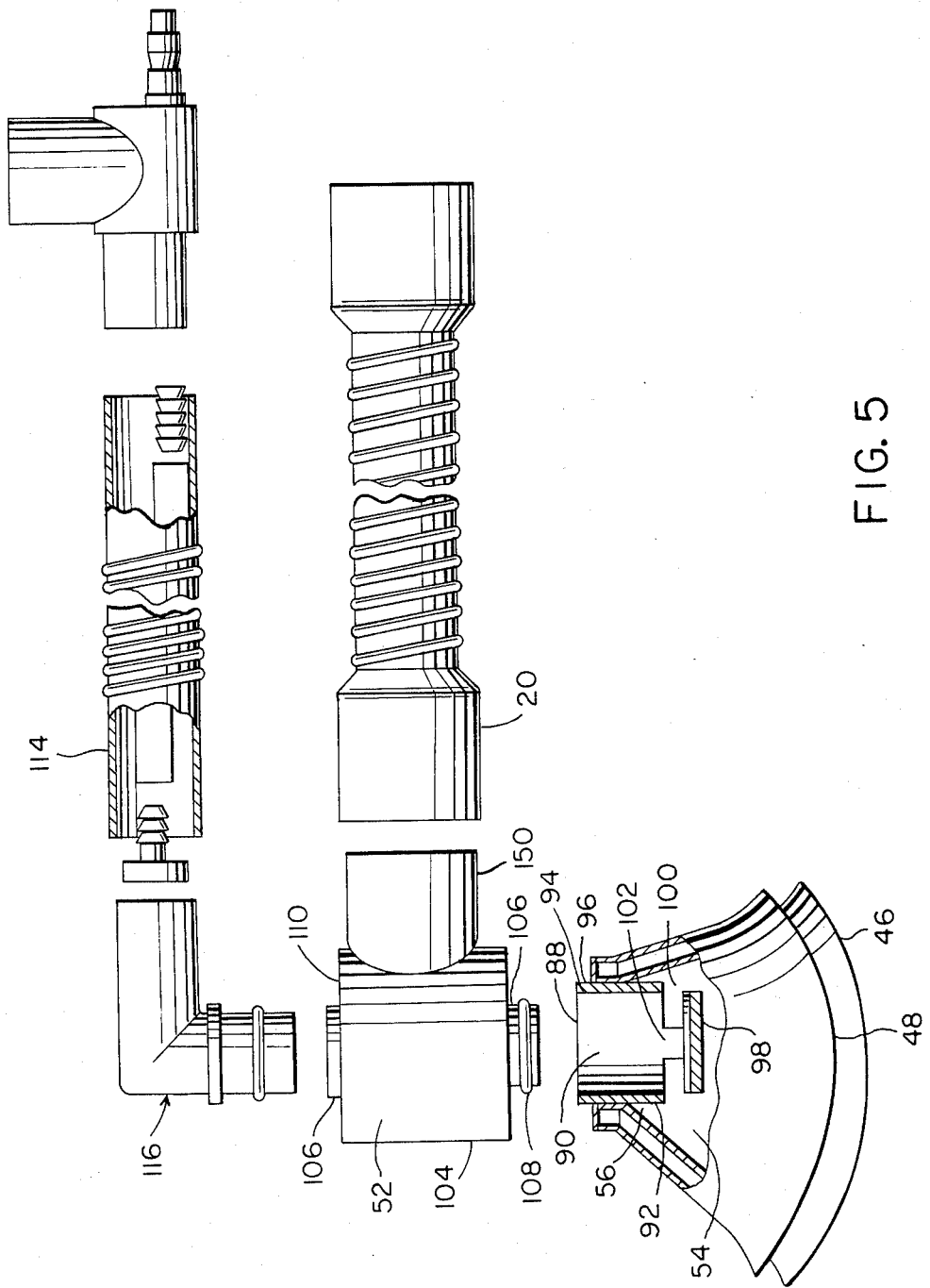
FIG. 5 is an exploded view of the assembly of the mask illustrated in FIG. 4 with a portion of the mask inner and outer body parts broken away.
Figure 6:
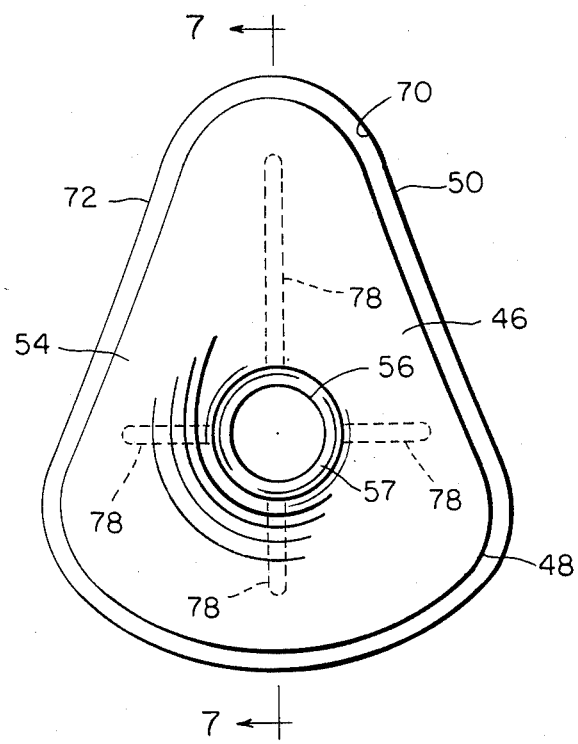
FIG. 6 is an axial view into the interior of the mask shown in FIGS. 4 and 5 as it faces the patient.

The internal structure of the mask assembly in accordance with the present invention is shown more clearly in FIGS. 5 and 6. Inner mask body 46 is a generally cup-shaped member that includes an inner wall 54 having an inner opening 56 therethrough, inner opening 56 having a central axis, and an outer opening 48 spaced from inner opening 56 and having an outline shaped to generally conform with the shape of a patient's face adjacent and surrounding the oral-nasal area. Outer opening 48 is defined by a continuous outer edge that is soft and flexible for comfortable engagement with the face of the patient, and that flares outwardly slightly for added comfort. Inner wall 54 of the inner mask body extends from inner opening 56 to outer opening 48 and is generally frustoconical when viewed in cross section. Preferably, inner mask body 46 is formed from a flexible material that can withstand sterilization temperatures, and, additionally, is preferably transparent or at least translucent in order to permit visual observation of the mouth and nasal area of the patient without the need to remove the mask from the patient's face. A particularly suitable material for the inner mask body is an elastomeric material, such as, for example, silicone rubber, which has thermal and chemical stability at high temperatures, which is chemically inert, and which provides the desired flexibility and transparency. As best seen in FIG. 6, inner wall 54 of the inner mask body includes a flat annular surface 57 surrounding opening 56, the purpose of which will hereinafter be explained.

Figure 9:
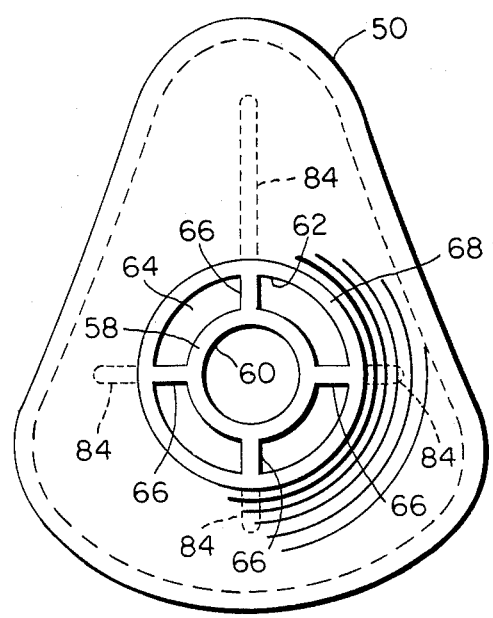
FIG. 9 is an axial view of the outer portion of the mask body in the opposite direction from the view of FIG. 6.

Spaced axially and transversely from and surrounding inner mask body 46 is outer mask body 50 that has a shape that corresponds generally with that of the inner mask body. Outer mask body 50 is also of a generally frustoconical, cup-shaped configuration, and includes an inner annular end wall 58 that defines an inner opening 60 that is substantially the same size as inner opening 56 of inner mask body 46, and a concentric outer opening 62 that defines an annular passageway 64 around inner opening 60. As shown in FIG. 9, annular end wall 58 separates inner opening 60 from annular passageway 64, and is concentrically supported within outer opening 62 of the outer mask body by means of four radially extending struts 66.

Figure 7:
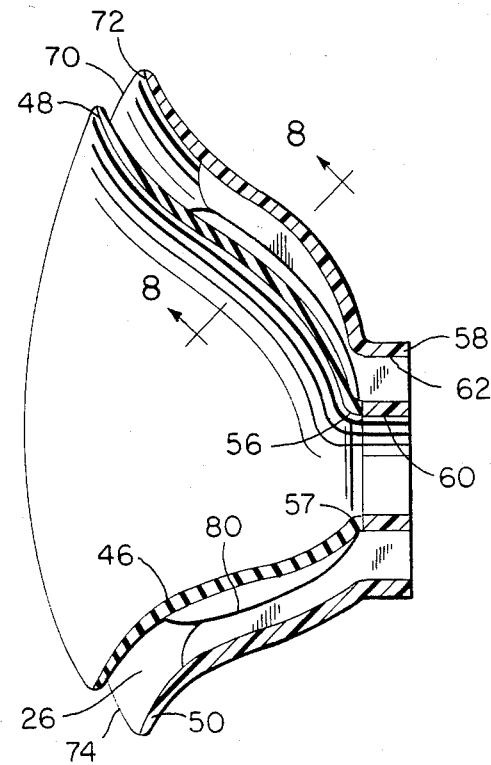
FIG. 7 is a cross-sectional view taken along the line 7—7 of FIG. 6.

Outer mask body 50 also includes an outer opening 70 defined by an outwardly flaring lip 72 and that generally conforms in shape with that of outer opening 48 in inner mask body 46. Outer opening 70 is spaced axially inwardly between outer opening 48 and inner opening 56 of inner mask body 46. As seen in FIG. 7, the outer openings of each of the inner and outer mask bodies are defined by an outwardly flaring lip, and the spacing between the two lips defines an annular entry slot 74 that communicates with space 76 between the inner and outer masks. Outer mask 50 is also preferably formed from a transparent material, again to permit visual examination of the oral-nasal area of the patient without the need to remove the mask from the patient's face, and it is preferably of a rigid construction. An example of a suitable material from which the outer mask body can be formed is polysulfone plastic manufactured by Union Carbide, a material that is rigid, strong, and easy to mold, and that can withstand sterilization temperatures. That material also exhibits chemical inertness, solvent resistance, and the desired transparency.

The inner and outer mask bodies are so sized that when the inner mask body is positioned within the outer mask body as shown in FIG. 7, the space 76 between the inner wall of the outer mask body and the outer wall of the inner mask body is of the order of about 3 to 4 mm. Additionally, in order to maintain a substantially continuous and uniform annular space between the two mask bodies and to prevent collapse of the inner mask body against the outer mask body, spacing means 78 (see FIG. 6) are provided between the two mask bodies. The spacing means radiate outwardly from the axis of the inner mask inner opening 56, and, as shown, are preferably oriented at an angle of 90° to each other, although other angular spacings can be employed, if desired, depending upon the number of spacing means employed.

Figure 8:
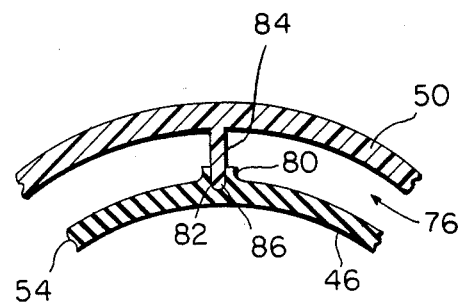
FIG. 8 is a cross-sectional view taken along the line 8—8 of FIG. 7.

The structure of the spacing means 78 is shown more clearly in FIGS. 7 and 8, and as there shown inner mask 46 includes four elongated protuberances 80 that extend outwardly from the outer surface of inner wall 54 thereof in a generally radial direction relative to the inner opening central axis, and commence at a point spaced from inner opening 56 and extend along the outer surface of inner wall 54 to a point between inner opening 56 and outer opening 48. Each of the elongated protuberances 80 includes a longitudinal linear depression in the form of a groove 82 (see FIG. 8) that extends substantially completely along the respective protuberances.

Outer mask body 50 includes a corresponding number of elongated ribs 84 that extend inwardly from and along the inner surface thereof and that also extend in a generally radial direction relative to the axis of inner opening 56. Ribs 84 have outer edges 86 that engage with grooves 82 in protuberances 80 on the inner mask body, and when engaged, ribs 86 and protuberances 80 serve to maintain the desired spacing between the inner and outer mask bodies. Additionally, the engagement of rib outer edges 86 with grooves 82 serves to prevent relative rotation between the inner and outer mask bodies when assembled and to maintain a substantially uniform spacing 76 therebetween. Thus, a substantially annular space extends substantially continuously between the inner and outer mask bodies. In addition to spacing the mask bodies from each other, ribs 84 and protuberances 80 also serve as a positioning means to properly align the inner and outer mask bodies during assembly of the mask.

The inner and outer mask bodies are held together by means of a center coupling 88, which is best seen in FIG. 5. Center coupling 88 includes a cylindrical body member 90 that includes an outwardly extending flange 92 to abut and engage with annular surface 57 (see FIG. 6) surrounding inner opening 56 of inner mask body 46. Spaced from outwardly extending flange 92 and at the opposite end of the cylindrical body is an external annular slot 94 that is adapted to receive a retaining ring 96, which can be an elastomeric O-ring. Annular slot 94 is so positioned relative to flange 92 that when a suitable retaining ring 96 is received therein, the inner and outer mask bodies are firmly held together as a result of flange 92 bearing against annular surface 57 and retaining ring 96 bearing against annular end wall 58. Further, by virtue of the flexibility of inner mask body 46, center coupling 88 can be pushed against inner mask body 46 so that flange 92 initially partially compresses the engaging annular surface 57 of the inner mask body so that annular slot 94 extends outwardly of inner opening 60 to facilitate application of the O-ring. Upon release of the compressive pressure, the O-ring firmly engages annular end wall 58 and flange 92 firmly engages surface 57 to tightly hold the inner and outer mask parts together in the proper orientation to maintain space 76 therebetween.

In addition to positioning the inner and outer mask bodies relative to each other, the center coupling also provides an additional function. As best seen in FIG. 5, an integral disk-shaped deflecting member 98 is carried by center coupling 88, and is spaced from flange 92 and from the opening defined thereby to provide a radially outwardly opening annular passageway 100 for gas that passes through cylindrical body member 90 in the direction of the mask opening 48. The disc-shaped deflecting member 98 has the same area as the inner opening 56 of inner mask body 46. Thus, deflecting member 98 deflects the incoming gas through an angle of about 90°. Deflecting member 98 is connected with cylindrical body member 90 by means of a pair of axially extending connecting ribs 102, only one of which is visible in FIG. 5. The purpose and operation of the deflecting means will be described in more detail hereinafter.

Coupling housing 52 includes a generally cylindrical outer body wall 104 and an inner concentric passageway defined by a cylindrical inner body wall 106, the latter having an outer surface of size adapted to be received in and to engage with the inner surface of cylindrical body member 90 in center coupling 88, and carries an external elastomeric O-ring 108 that is retained in a circumferential slot (not shown) for sealing engagement therewith. Inner body wall 106 extends through the top wall 110 of the coupling housing and is adapted to receive a connector 116, such as the right angle connector illustrated in FIG. 5, which is connected to a suitable tube 114 through which anesthetic gas can be introduced into the interior cavity of the inner mask member 46 and from which exhaled gas from the patient can be withdrawn.

Figure 10:
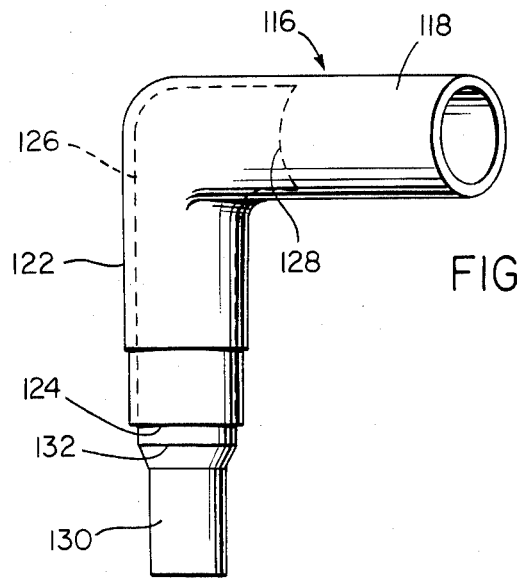
FIG. 10 is a side view of a branched connector for introducing anesthetic gas into a mask and for withdrawing exhaled gas therefrom, including a partition member to separate the flow passages and extend the two branches from the point of separation to a common outlet end.
Figure 11:
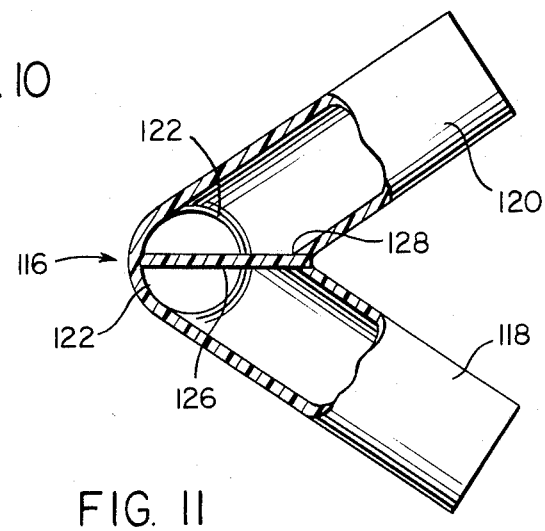
FIG. 11 is a top view, partially broken away, of the connector of FIG. 10.

The introduction of the anesthetic gas into the inner mask cavity and the withdrawal of the exhaled gas therefrom can be accomplished by means of a pair of separate hoses that interconnect with respective defined channels in an angle connector 116, as shown in FIGS. 10 and 11. Connector 116 includes two branch pipes 118, 120 that are disposed with their axes in a V-shape at an acute angle and that merge into a single connecting head 122 that is at a right angle bend relative to the axes of pipes 118, 120 to merge the two pipes into one pipe that engages with the coupling housing of the anesthetic mask. In the angle connector shown, there is a space that is defined by the volume between the junction of pipes 118, 120 and the outlet 124 of connecting head 122. The socalled "dead space" includes the space within the angle connector and the portion of the interior of the mask that is not filled by the patient's face. The dead space is undesirable in that a certain quantity of the exhaled gas from the patient will not be withdrawn into the exhaled gas tube, but will remain within the dead space and will be reinhaled together with a fresh supply of anesthetic gas. The dead space thus results in dilution of the anesthetic gas, and what is even more objectionable, the reinhalation of exhaled gas having a high content of carbon dioxide. The resulting incomplete ventilation could cause an undesirable increase in the carbon dioxide concentration level within the mask.

The total dead space volume can be reduced by providing a partition 126 within angle connector 116 and extending from the junction 128 of pipes 118 and 120 to at least the outlet 124 to provide an extension of the separate spaces within pipes 118, 120. Preferably, partition 126 includes an extension 130 that extends beyond opening 124 so that upon assembly of connector 116 and the coupling housing 52, the extension projects into the opening within inner cylindrical body wall 106 in the coupling housing to divide it into two separate passageways. In order to reduce the need of storing different types of connecting devices, depending upon the type of mask employed, the extension is provided with a score line 132 which, when the connector is used in masks without any means for extracting leaking gas, permits breaking off the unneeded part of the extension.

In addition to its separation function, the partition and the extension can be used as moisture-transferring means between the passage for exhaled gas and the passage for anesthetic gas, by equipping it with openings or recesses through which moisture taken up by a suitable moisture-absorbing layer facing the passage for exhaled gas can be transferred to a moisture-dissipating layer facing the passage for anesthetic gas.

Figure 12:
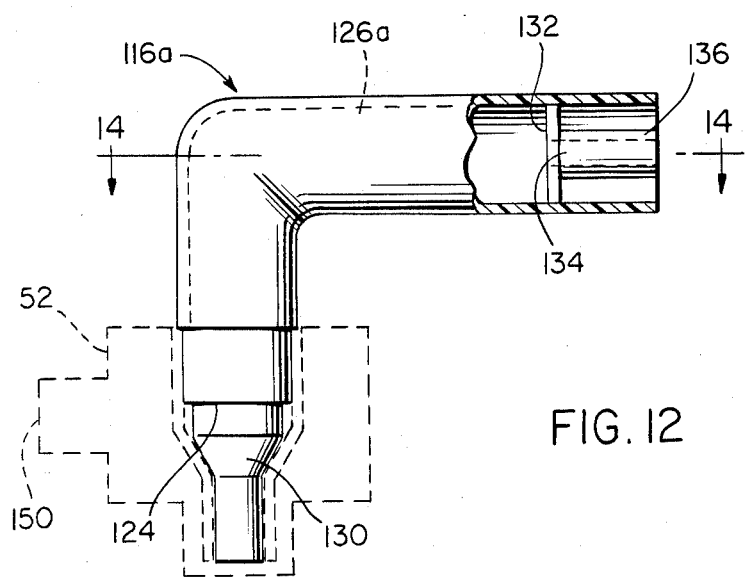
FIG. 12 is a fragmentary side view of another form of connector for introducing anesthetic gas and for withdrawing exhaled gas wherein coaxial tubes are employed for the anesthetic gas and for the exhaled gas.
Figure 13:
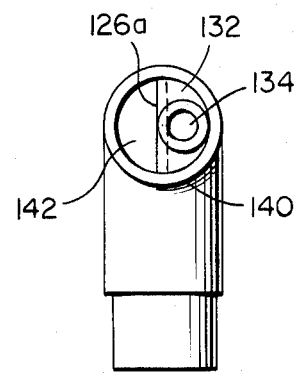
FIG. 13 is an end view of the connector of FIG. 12.
Figure 14:
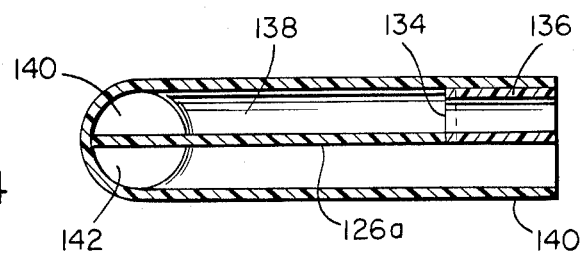
FIG. 14 is a cross-sectional view of the connector of FIG. 12 taken along the line 14—14 thereof.

As an alternative to the branched connector illustrated in FIGS. 10 and 11, a concentric tube arrangement can also be provided. Such a concentric tube arrangement is illustrated in U.S. Pat. No. 3,856,051, which is the standard, so-called Bain system, the disclosure of which is hereby incorporated by reference the same as if fully set forth herein. The connector embodiment illustrated in FIGS. 12 through 14 is for use with a coaxial supply and withdrawal tube of the Bain type wherein an inner tube that carries the anesthetic gas is coaxially disposed within an outer tube through which the exhaled gas is removed. In this embodiment, connector 116a includes a semicircular transverse wall 132 having an opening 134 adapted to provide communication between inner tube 136 and channel 138. Outer tube 140 is connected to the end of connector 116a in a suitable manner and is in direct communication with the other channel 142 through the semicircular opening at transverse wall 132. Partition 126a extends from transverse wall 132, through the connector, to the opening 124 and extends beyond the latter into connecting housing 52 to eliminate the dead space in the connecting device.

An annular passageway is defined between the inner body wall 106 and the outer body wall 104 of coupling housing 52, and is connected to extraction tube 20 by means of an outlet connection 150 (see FIG. 5). Extraction tube 20 is in communication with space 76 between the inner and outer mask bodies through the annular passageway 64 in the outer mask body and the annular passageway in coupling housing 52. The extraction tube is adapted to be connected to a source of vacuum to cause a lower pressure to exist in the space between the inner and outer mask bodies, to thereby draw in, collect, and remove the leakage anesthetic gas that passes outside of the inner mask body during use. Additionally, and as is apparent from the parts and their relationship as illustrated in FIG. 5, coupling housing 52 is rotatable relative to the inner and outer mask assembly for convenient positioning of the extraction tube. Further, the gas introduction tube and the exhaled gas tube are also pivotally connected to the coupling housing for the same reason.

In operation, the anesthetic gas tube is connected to a suitable supply of the desired anesthetic gas and a regulated amount of gas at a desired pressure is permitted to flow thereinto. Because the anesthetic tube is in communication only with the interior of the inner mask body, an anesthetic atmosphere is provided within that cavity. Similarly, the exhaled gas tube is also connected to the cavity defined by the inner mask body, and is at a lower pressure so that excess anesthetic gas as well as gas exhaled by the patient are withdrawn from the inner mask body. The withdrawal of exhaled gas is necessary to minimize reingestion of the exhaled gas, particularly carbon dioxide.

Any anesthetic gas that escapes between the patient's face and outer opening 48 of inner mask body 46 is drawn into space 76 between the inner and outer mask bodies through slot 74 by virtue of the reduced pressure therein when the extraction passage is in communication with a source of vacuum, such as a fan, or the like. Additionally, the transparency of the inner and outer mask bodies permits direct visual observation of the patient's nose and mouth, to thereby permit the detection of changes in color of the patient's lips, indicative of an oxygen deficiency, and also to detect vomiting or other problems without the necessity for frequently removing the mask from the patient, with consequent escape of anesthetic gas.

Figure 15:
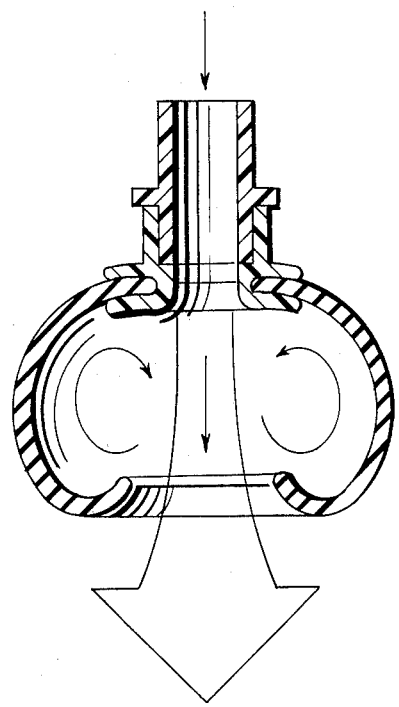
FIG. 15 is a schematic view showing the structure and the gas flow path of a prior art mask device.
Figure 16:
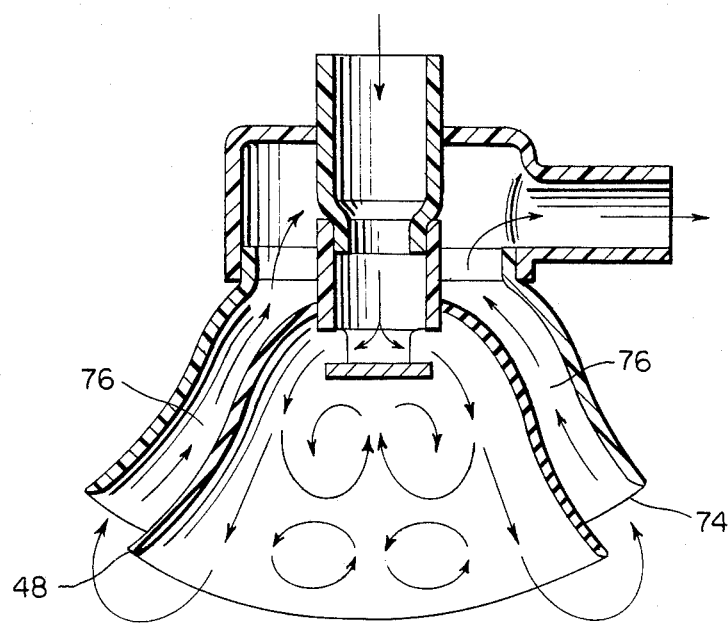
FIG. 16 is a schematic view showing the structure and the gas flow paths of a mask device in accordance with the present invention.

The operation of the prior art mask structure and of the mask of the present invention is illustrated in FIGS. 15 and 16. As shown in FIG. 16, in the mask according to the present invention the deflection means causes the incoming anesthetic gas to be deflected radially outwardly, relative to the axis of the center coupling, and to generally follow the interior surface of the inner mask body. Additionally, because of the radial flow, a reduced pressure area is generated on the side of the deflection means that faces the patient, thereby inducing turbulent flow and eddy currents, which serve to cause the anesthetic gas to be contained within the inner mask body, or just slightly beyond the outer edge thereof, by virtue of the reduction in the axial velocity of the anesthetic gas by the presence of the deflection means. In effect, the mask according to the present invention provides a turbulent bubble of anesthetic gas contained largely within the cavity of the inner mask body but that can extend slightly outwardly beyond it, the bubble including turbulently flowing gases that define an anesthetic gas zone within the inner mask body. As also seen in FIG. 16, gases that may escape beyond the outer edge 48 of the inner mask body are sucked into the slot 74 and space 26 between the inner and outer mask bodies by virtue of the reduced pressure therein caused by the connection thereof to a source of vacuum, a fan, or the like. Thus, gases that pass beyond the inner mask body are collected, and do not contaminate the surrounding atmosphere.

In distinct contract to the operation of the mask according to the present invention as shown in FIG. 16, the prior art mask device as illustrated in FIG. 15 operates in such a way that although some small turbulence and eddy currents may exist in the interior of the mask, the major portion of the anesthetic gas flow is directed toward the center of the outer opening in the mask, and thus the gas flow is directed outwardly of the mask, and it more readily escapes from the mask into the surrounding atmosphere and thereby serves to contaminate the same. Although the prior art mask device functions reasonably well when it is in contact with the patient's face, removal of the mask from the patient, such as, for example, for periodic checking of the patient's oral-nasal area, results in considerable escape of gas into the surrounding atmosphere and thereby pollutes the same, whereas with the mask of the present invention, as illustrated in FIG. 16, the mask can be removed entirely from the patient's face, without the need for reducing or turning off the gas flow, and without any excessive escape of gas into the surrounding atmosphere. In fact, tests of the operation of a mask in accordance with the present invention have shown a reduction of from 80% to 90% in the contamination of the operating room atmosphere by anesthetic gases when compared with the performance of the prior art mask such as illustrated in FIG. 15. The tests showed that the anesthetist's exposure to nitrous oxide was reduced by about 90%. Further, in all cases in which the prior art mask illustrated in FIG. 15 was utilized, the operating room atmosphere was contaminated by anesthetic gas to an amount in excess of 25 ppm, whereas when the mask in accordance with the present invention was used, in 13 out of 16 cases in which nitrous oxide was used as the anesthetic gas, the level of anesthetic gas contamination in the operating room was reduced to a level below the NIOSH-recommended level of 25 ppm.

In addition to the reduction in anesthetic contamination of surrounding air, the present invention was also found in those tests to be capable of operation at a low noise level of around 45 db(A) in the low frequency range, where noise is regarded to be most disturbing. That noise level was at an evacuation flow rate of 35 m³/h through the slot between the outer and inner masks.

In addition to the applicability of the present invention to introduction of anesthetic gas through the patient's oral-nasal area, it has also been found that a mask in accordance with the present invention can be utilized with an endotracheal tube. In that application, the mask is disconnected from the gas delivery and exhaled gas tubes, and the inner tube of the coupling housing is attached to the endotracheal tube. As a result, the anesthetics that escape around a leaking endotracheal tube can be effectively collected by virtue of the double wall mask construction of the present invention.

Although particular embodiments of the present invention have been illustrated and described, it will be apparent to those skilled in the art that various changes and modifications can be made without departing from the spirit of the present invention, and it is intended to cover in the appended claims all such changes and modifications that fall within the scope of the present invention.

What is claimed is:

1. A mask for administering anesthetic gas, said mask comprising:
   (a) an inner, cup-shaped mask body defining a cup-shaped cavity, said inner mask body including an inner opening having a central axis, an outer opening spaced from said inner opening along said central axis, and a continuous sidewall extending from said inner opening to said outer opening, said sidewall having a flexible edge defining the outer opening, said outer opening having a larger area than said inner opening and a shape adapted to engage the face of a patient in substantially gas-tight sealing relationship outwardly of the patient's nose and mouth;
   (b) an outer, cup-shaped body including an inner opening having a central axis, an outer opening larger than and spaced from said inner opening along said central axis and a second continuous sidewall having a shape corresponding with the shape of said inner body extending from said inner opening to said outer opening, said continuous sidewall having an outer edge defining the outer opening of the outer body;
   (c) said outer body and said inner body being arranged with said outer body surrounding but spaced from said inner body to define an extraction passageway therebetween bounded by the sidewalls of said inner and outer bodies, the outer opening of said outer body positioned relative to said central axis between the outer and inner openings of said inner body to thereby define an annular extraction slot between the edge of said inner body and the edge of said outer body, said inner opening of said outer body surrounding said inner opening of said inner body and communicating with said extraction slot through said extraction passageway;
   (d) deflecting means supported in said cup-shaped cavity opposite said inner opening for deflecting incoming fluid passing through said inner opening of said inner body outwardly at an angle to said central axis; and
   (e) coupling means for connection to said inner opening of said outer body to provide communication with an exhaust system and for connection to said inner opening of said inner body to provide communication with a source of pressurized anesthetic gas and with an exhaust system to withdraw gas exhaled by the patient.

2. A mask in accordance with claim 1 wherein the outer mask body is of a rigid material.

3. A mask in accordance with claim 1 wherein the inner mask body is of a flexible material.

4. A mask in accordance with claim 1 wherein the outer mask body is made of a rigid material and the inner mask body is made of a flexible material.

5. A mask in accordance with claim 1 wherein the inner and outer mask bodies are composed of a transparent material.

6. A mask in accordance with claim 1 wherein the outer mask body is made of transparent material, and the inner mask body is made of translucent material.

7. A mask in accordance with claim 1 wherein the inner and outer mask bodies each have the same overall shape.

8. A mask in accordance with claim 1 wherein the spacing between the inner and outer mask bodies is about 3 to 4 mm.

9. A mask in accordance with claim 1 wherein the edges of both the inner and outer mask bodies flare outwardly.

10. A mask in accordance with claim 1 including spacing means to space the inner and outer mask bodies from each other a predetermined distance.

11. A mask in accordance with claim 10 wherein said spacing means includes radially inwardly extending ridges formed on the inner surface of the outer mask body engaging with the outer surface of the inner mask body.

12. A mask in accordance with claim 11 wherein four ridges are peripherally disposed about said central axis approximately 90° apart and extend from the inner opening of the outer mask body and terminate inwardly of the outer opening thereof.

13. A mask in accordance with claim 11 wherein said spacing means further includes elongated slots formed on the outer surface of the inner mask body engaging with the ridges of the outer mask body to hold the mask bodies spaced apart and to prevent relative rotation therebetween.

14. A mask in accordance with claim 13 wherein the elongated slots are defined by radially outwardly extending ridges formed on the outer surface of the inner mask body.

15. A mask in accordance with claim 1 wherein said deflecting means is in the form of a disk whose center point is coaxial with said central axis.

16. A mask in accordance with claim 15 wherein the disk is the same size as that of the inner opening of the inner body.

17. A mask in accordance with claim 1 wherein said coupling means comprises a connector that includes a tubular connecting head terminating in an opening and a pair of branch pipes extending from said connecting head, one of said branch pipes adapted to be in communication with the source of pressurized anesthetic gas and the other branch pipe adapted to be in communication with a source of reduced pressure to withdraw gases exhaled by the patient, partition means extending from said branch pipes through said connecting head and through said opening for separating the flow paths of the anesthetic gas and of the exhaled gas and coupling housing means for fluidically connecting said inner opening of said inner body to said connector opening and said inner opening of said outer body with the exhaust system.

18. A mask in accordance with claim 17 wherein said branch pipes extend individually from said connecting head.

19. A mask in accordance with claim 18 wherein said branch pipes are disposed with their axes in a V-shape at an acute angle.

20. A mask in accordance with claim 17 wherein said partition means includes a transfer layer to permit the transfer of humidity from the exhaled gas passageway to the anesthetic gas passageway.

21. A mask according to claim 1 further comprising interconnecting means for interconnecting the sidewalls at the inner openings thereof.

22. A mask according to claim 21, wherein said deflecting means extends from the interconnecting means.

23. A mask according to claim 22, wherein the interconnecting means includes first means for engaging a part of the inner mask body and seal means for engaging a part of the outer mask body.

* * * * *